United States Patent [19]

Valentine et al.

[11] Patent Number: 4,925,047
[45] Date of Patent: May 15, 1990

[54] MULTIPURPOSE SHAPED PITCHER AND SURGICAL KIT AND WRAP SYSTEM

[76] Inventors: A. H. Llynn Valentine, 15634 View Ridge La., Granada Hills, Calif. 91344; William L. Noack, 83 N. Calle Vista, Camarillo, Calif. 93010

[21] Appl. No.: 321,224

[22] Filed: Mar. 9, 1989

[51] Int. Cl.⁵ .............................. B65D 6/00
[52] U.S. Cl. ........................ 220/23.83; 220/83; 206/570
[58] Field of Search .......... 220/23.83, 23.86, 83, 220/94 A; 206/546, 570, 223, 436

[56] References Cited

U.S. PATENT DOCUMENTS

| | | | |
|---|---|---|---|
| 2,613,517 | 10/1952 | Frantz | 220/23.83 X |
| 2,626,737 | 1/1953 | Pitz | 220/23.83 X |
| 2,932,437 | 4/1960 | Wilcox | 220/94 A X |
| 3,385,465 | 5/1968 | Bliss | 220/23.83 X |
| 4,221,295 | 9/1980 | Tuchband et al. | 206/570 X |
| 4,241,833 | 12/1980 | Luebcke | 206/570 |
| 4,483,455 | 11/1984 | Prophet, Jr. et al. | 220/23.83 |

Primary Examiner—Steven M. Pollard

[57] ABSTRACT

The surgical kit contains a pair of nested circular basins, one or more nested kidney-shaped pans, and one or more nested heart-shaped pitchers. Other surgical needs may also be packed in the basin. A drape having a sterile side is wrapped around the basin with the sterile side inward and a double fold therein. The basin is placed in a ring stand, and when the drape is unwrapped, the sterile side is outward. When there are two nested basins, a double ring stand is employed and the double fold is pulled out to cover the entire double ring stand.

20 Claims, 4 Drawing Sheets

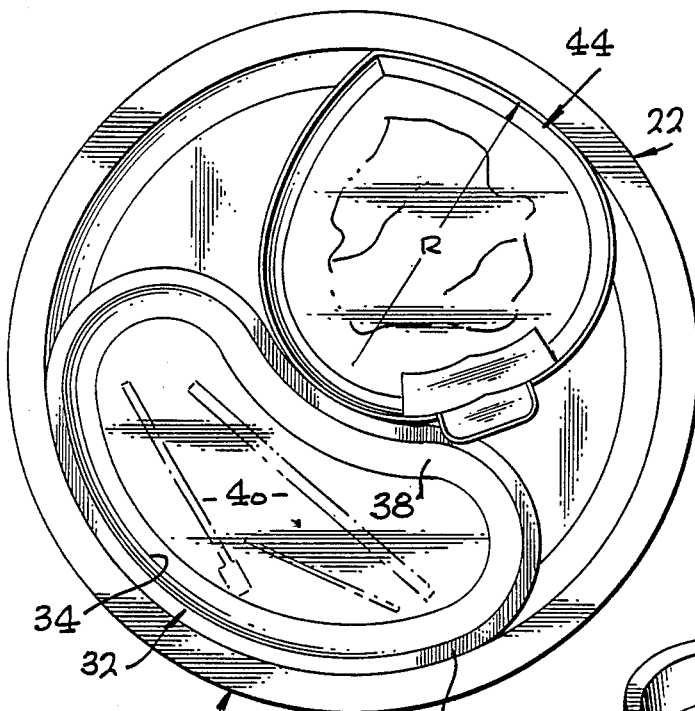
FIG. 1
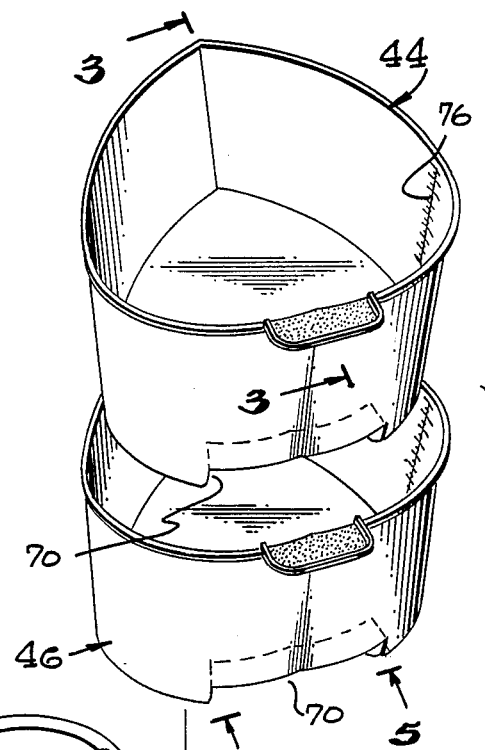
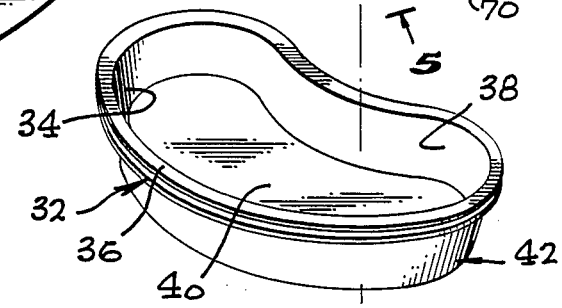
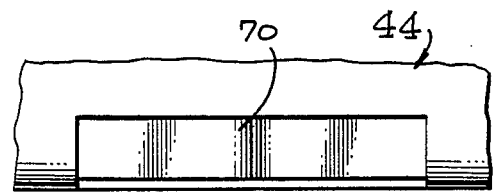
FIG. 5
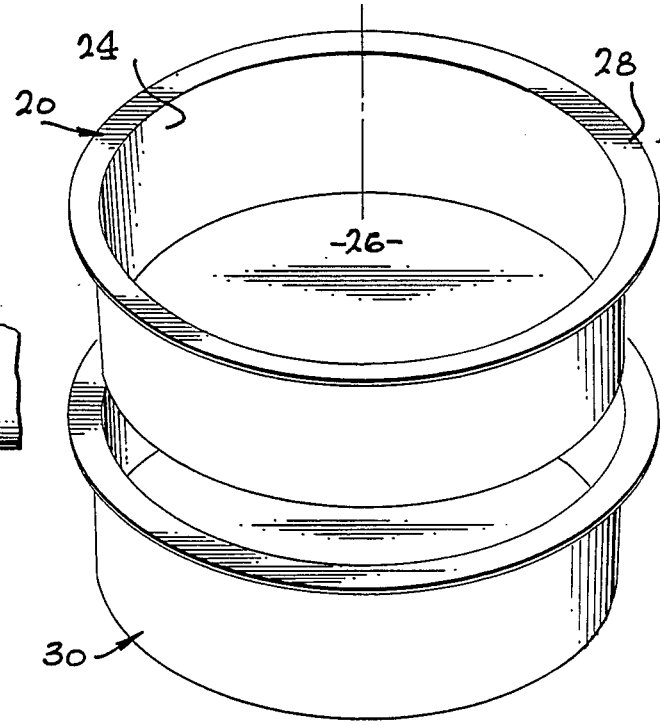
FIG. 2

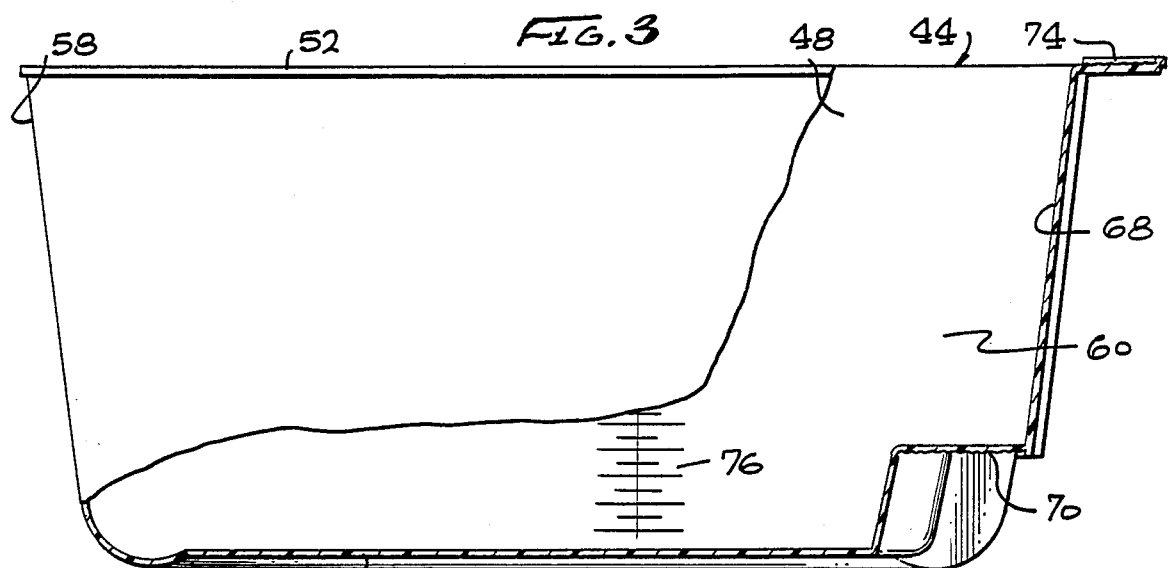
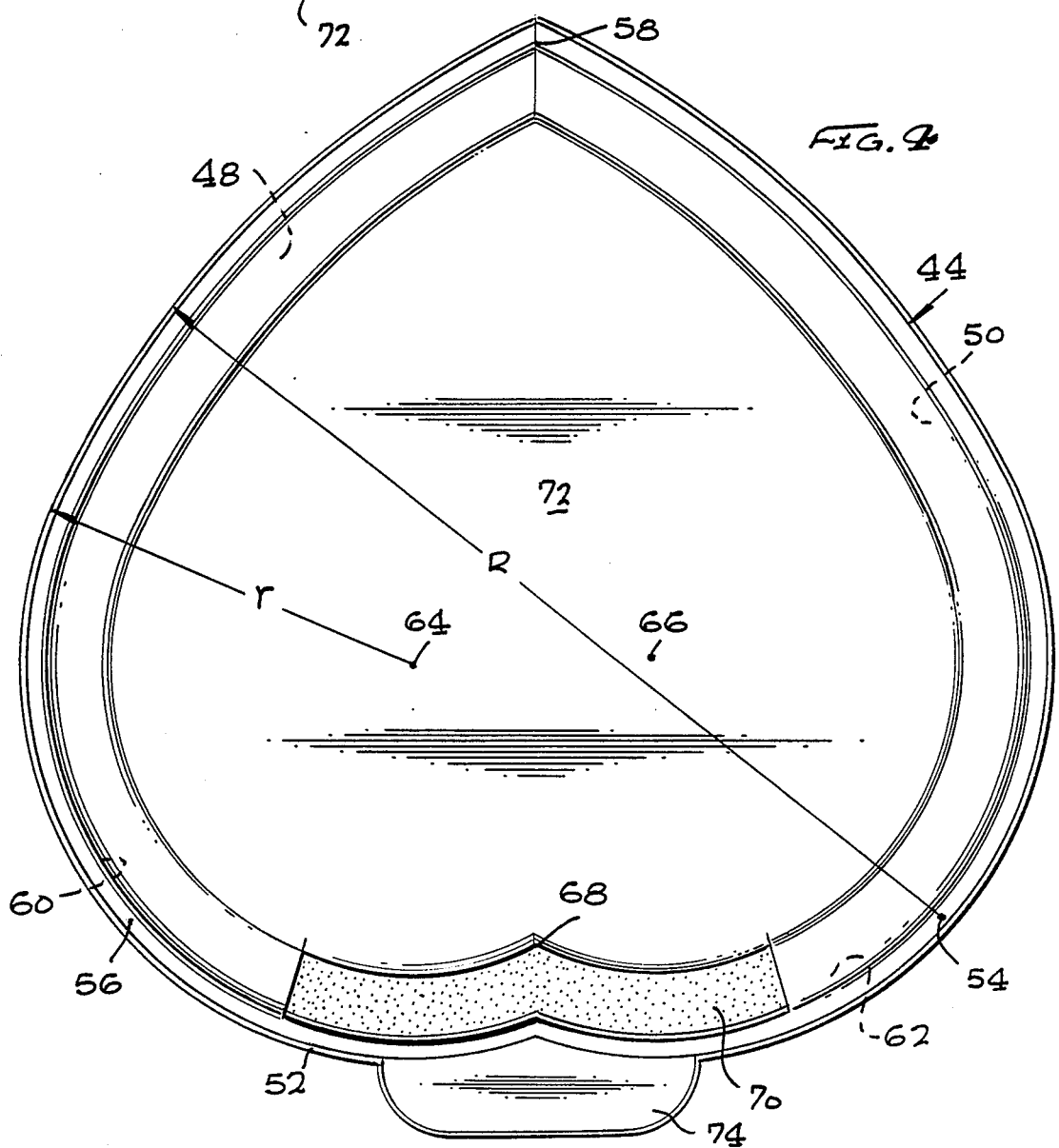

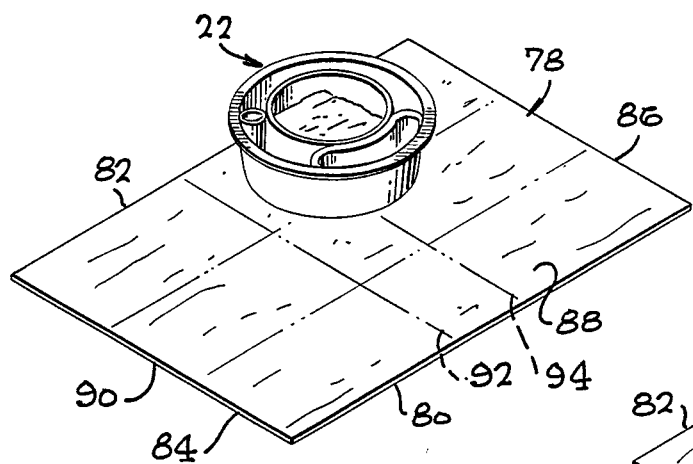
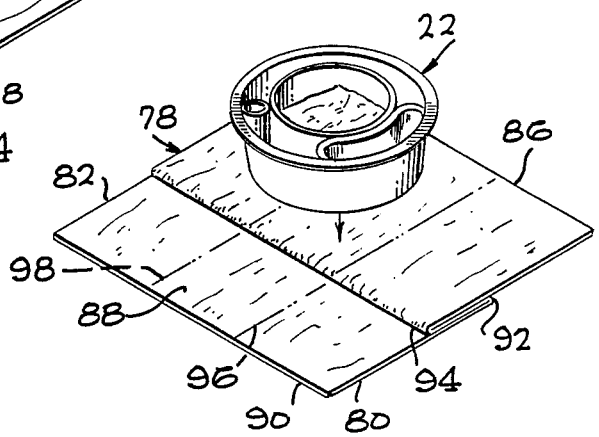
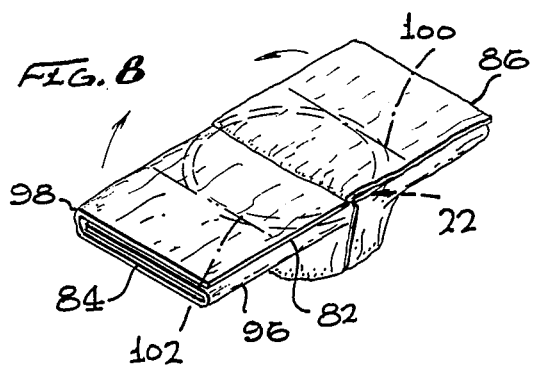
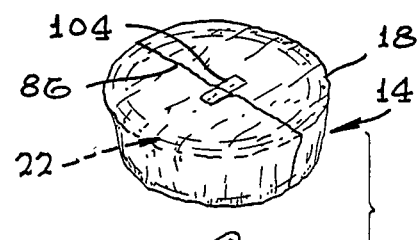
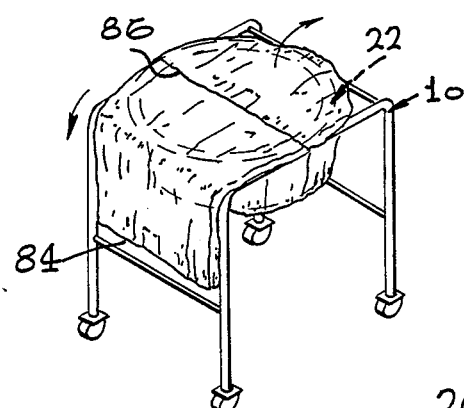
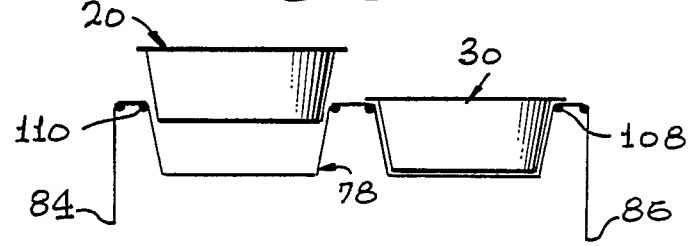

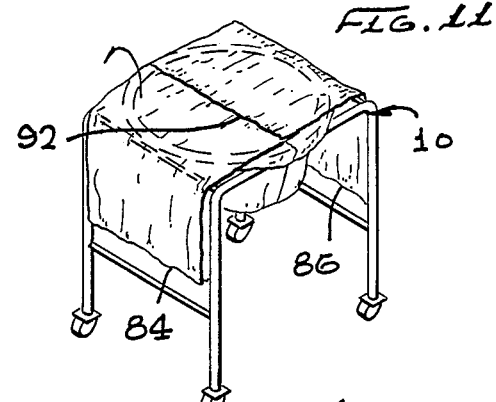
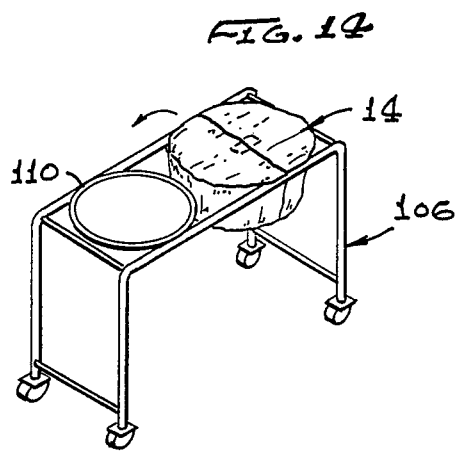
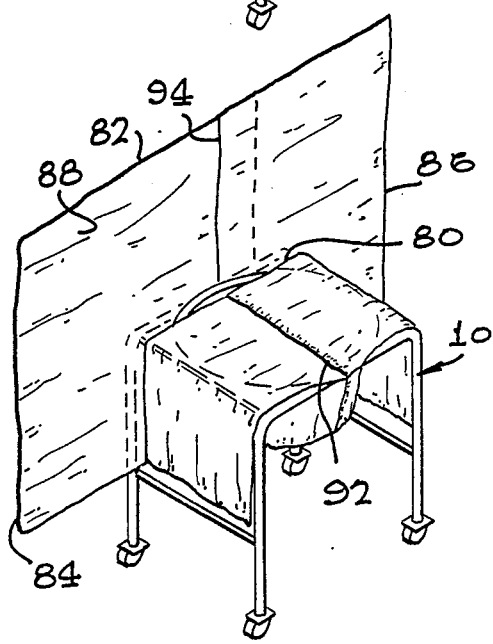
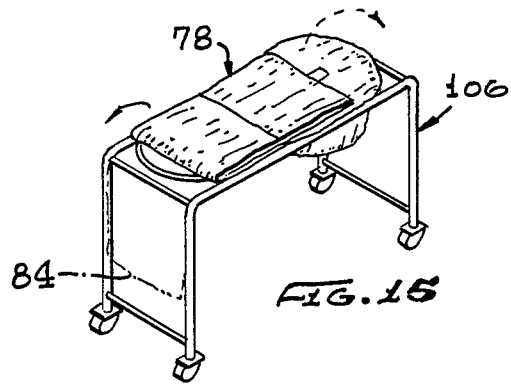
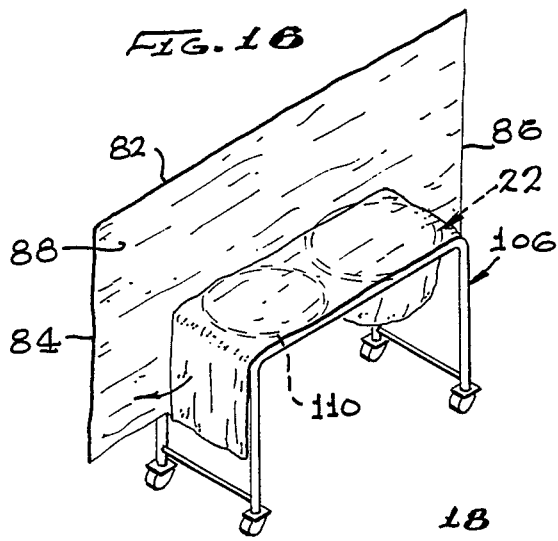
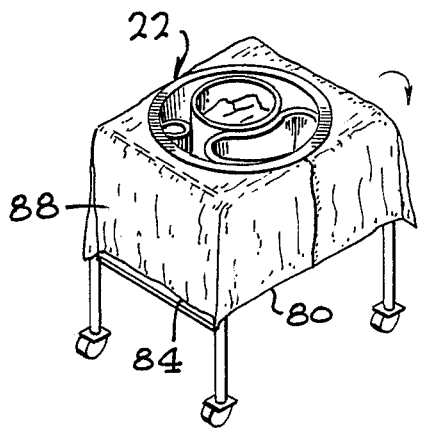
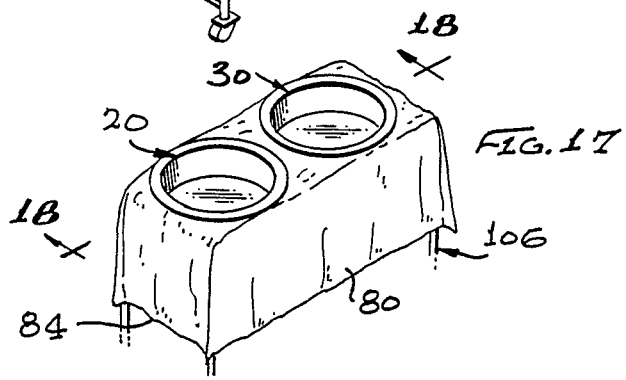

MULTIPURPOSE SHAPED PITCHER AND SURGICAL KIT AND WRAP SYSTEM

FIELD OF THE INVENTION

This invention is directed to a kit having therein at least some of the materials required for a particular surgical procedure, including a basin, a pitcher within the basin, and a drape wrapped around the basin and pitcher therein so that when the drape is unwrapped, the basin is exposed and the sterile side of the wrap is presented.

BACKGROUND OF THE INVENTION

Modern operating room procedures employ surgical kits which contain therein at least some of the equipment needed in association with the procedure. When a particular surgical procedure is defined, the equipment is brought together and is wrapped and sterilized. This kit is taken into the operating room to provide at least some of the equipment and materials needed for the procedure. Different surgeons and different procedures require different sets of material, and thus a variety of kits is available.

In connection with such kits, it is necessary to provide compact packaging so as to minimize storage space before use, and provide equipment which is of the desired utility for the surgical procedure. These material or equipment items are preferably of such nature as to be disposable so that they are destroyed after use. In order to maximize utility, it is desirable to provide a kit which has multiple use capability.

SUMMARY OF THE INVENTION

In order to aid in the understanding of this invention, it can be stated in essentially summary form that it is directed to a multipurpose shaped pitcher and a surgical kit and wrap system. The pitcher is symmetrically heart-shaped with a larger radius to fit the inside of a basin in which it is packed and a smaller radius to fit against the kidney-shaped pan also within the same basin. The wrapped system includes a fold in a drape with a drape wrapped around the basin. The drape is sized to unwrap and cover a single ring stand when the fold is in place and to cover a double ring stand when the fold is pulled out of the drape.

It is thus an object and advantage of this invention to provide a shaped pitcher which readily fits within a surgical kit including a basin and is sized so that it can be readily handled in one hand and pours from a pointed spout defined by its multi-radius configuration.

It is another object and advantage of this invention to provide a wrap system for a surgical kit wherein the drape employed in the wrap system has a double fold so that when the double fold is left in place, the drape is of a size to fit over a single ring stand, and when the double fold is pulled out, the drape is sized to fit over a double ring stand.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1 is a plan view of the unitary surgical kit including a multipurpose shaped pitcher in accordance with this invention.

FIG. 2 is an exploded isometric view of the surgical kit.

FIG. 3 is an enlarged section of the multipurpose shaped pitcher of this invention, as seen generally along the line 3—3 of FIG. 2.

FIG. 4 is a plan view of the multipurpose shaped pitcher.

FIG. 5 is an enlarged detail of the multipurpose shaped pitcher, as seen generally along the line 5—5 of FIG. 2, with parts broken away.

FIG. 6 is an isometric view showing a surgical kit projected above the wrapping drape in which it is to be wrapped.

FIG. 7 is a similar view showing the surgical kit above the wrapping drape after the first pair of folds is made in the wrapping drape.

FIG. 8 is similar to FIG. 7 showing a further subsequent step in the wrapping of the basin.

FIG. 9 shows the wrapped basin in association with the ring stand.

FIG. 10 is a similar view showing the wrapped basin placed in the ring stand with the unwrapping commencing.

FIG. 11 is a similar view showing the next unwrapping step.

FIG. 12 is a similar view showing a further unwrapping step.

FIG. 13 is a similar view showing the basin fully unwrapped.

FIG. 14 is an isometric view showing a surgical kit placed within a double ring stand.

FIG. 15 is a similar view showing the beginning of the unwrapping of the drape.

FIG. 16 is a similar view showing the next-to-the last wrapping step.

FIG. 17 is a similar view showing the completion of the unwrapping.

FIG. 18 is a section taken generally along the line 18—18 showing the two basins on the wrap on a double ring stand.

DESCRIPTION OF THE PREFERRED EMBODIMENT

Single ring stand 10 is shown in FIG. 9. It has a ring 12 at the top for the support of a surgical kit. The wrapped kit is generally indicated at 14 in FIG. 9. Legs 16 of the ring stand support the ring 12 above the floor at a convenient height for use in surgery. The wrapped kit 16 includes the wrapping 18, which serves as a ring stand drape when unwrapped, as later described.

FIGS. 1 and 2 show circular basin 20, which is the largest part of the surgical kit, which is generally indicated at 22 in FIGS. 1 and 2. The basin 20, as seen in FIG. 2, has tapered circular side walls 24 which terminate in a bottom 26. The basin preferably has a top rim 28. The circular side walls have a radius R at the top rim and are tapered for convenient molding and for nesting of several such basins. In FIG. 2, the basin 20 is shown as being raised above an identical basin 30 in which it had been nested and raised for this exploded view. The outer diameter of the basins 20 and 30 underneath the rim is such as to fit loosely within the ring 12 of ring stand 10.

Kidney-shaped pan 32, seen in FIGS. 1 and 2, is shaped to fit within the basin. It has an outer wall 34 surmounted by rim 36 and an inner wall 38. The walls are closed by bottom 40. The walls are of the same taper as the side wall 26 of the basin, and the curvature of the outer wall 34 is on the same center as the curvature of the basin side walls so that the rim 36 engages directly against the basin side wall. The depth of the pan is less than the depth of the basin so that the pan may fit within the basin to provide space within the pan and above the pan for the packing of additional materials, such as clamps, sponges, surgical drapes, and/or surgical instruments. Several surgical instruments are shown in dashed lines within the pan in FIG. 1. For the case where two such pans are helpful, for example when there are two basins, a second pan 42 has the pan 32 nested therein.

Pitcher 44, seen in FIGS. 1, 2, 3 and 4, is the upper pitcher which nests within the lower pitcher 46, seen in FIG. 2, provided when two such pitchers are helpful or required. The pitchers 44 and 46 are identical, and their side walls are sufficiently conical so as to aid in molding and permit nesting. As is seen in particular in FIGS. 3 and 4, pitcher 44 has side walls 48 and 50 which are the same curvature R so that they fit within and against the interior of the basin side walls, as is seen in FIG. 1. A very small rim 52 is provided on the pitcher side walls so that they fit closely within the circular basin. The side walls 48 and 50 are respectively curved around the radius center points 54 and 56 shown in FIG. 4. Since the side walls 48 and 50 are of the same radius R but about separated center points, the curved side walls meet at a pouring point 58. The side walls 60 and 62 are respectively curved around center points 64 and 66 on radius r. The tangent point between the two curves is substantially at center points 54 and 56 to provide a smooth curve. The radius r is substantially the same as the curvature of the inner wall of kidney-shaped pan 32, and the total distance across the pitcher 44 and kidney-shaped pan 32 is substantially equal to the distance across the basin 22 so that when the smaller curved side wall of the pitcher fits within the curve of the inner wall 38 of the pan, the pitcher and pan fit closely within the basin to conserve space.

The curved walls 60 and 62 may join in straight section tangent to both of the curves, but is preferably indented to define the heart shape shown in FIG. 4. This heart shape provides an inwardly directed point 68 which serves as a tactile reference point for grasp and determining the center of the back of the pitcher. FIG. 4 is a bottom view and shows the indented surface 70 towards the bottom 72 of the pitcher. This indented surface is large enough to receive the tips of the four fingers of the hand which is used to pick up the pitcher. The indented surface 70 is roughened, as seen in FIG. 4. Complementing the indented surface is grasp flange 74, which extends outward as a rim at the back of the pitcher above the indented surface 70. Grasp flange 74 is sufficiently large as to be grasped by the thumb and is also roughened, as is seen in FIG. 2.

Pitcher 44 may be transparent or opaque. It has molded on the surface thereof graduations 76. Preferably, these graduations are formed on both sides of the pitcher, as seen in FIG. 2. When transparent, the graduations can be read from both the inside and out. When opaque, the graduations are preferably formed on the inside surface so as to accurately read the liquid level therein. Two pitchers are furnished with each kit, and they may be of different colors to indicate different contents. For example, one can be furnished in transparent material to act as a graduate, and the other may be furnished of opaque material to serve as a sponge bowl. The pitchers are suitable for various operating room purposes. For example, they may be used as a sponge bowl, a saline bowl, or as a graduated pitcher. The pitcher is of such size as to adequately hold sponges and sufficient fluid as to be useful and avoid danger of spillage. The graduations provide accurate measurement of contents. Furthermore, the provision of the graduations on two opposite sides allows visual inspection of the fluid level without having to turn the pitcher. The pouring spout 58 ensure the capability of pouring a steady, accurate stream of liquid, and the indented grasp surface and the grasp flange are anatomically designed to permit safe handling of the pitcher. Furthermore, its low height resists tipping of it is bumped.

As discussed above, the kit 22 can contain a variety of materials and equipment which are useful in surgery. Most of the items are included in duplicate so that enough will be available for the surgery, and even though more may be available than is absolutely required, stock and supply of the kits is more readily achieved. For example, two basins are preferably included, two kidney-shaped pans, and two pitchers are preferably included. The pitchers may be employed as graduates for the receipt and dispensing of liquid or may be employed as sponge bowls. For this multiple usage, they may be made of visually different material so that the different usage is readily distinguished. For example, one may be made of a transparent material, and another of opaque to distinguish these utilizations. Various other materials useful in the operating room are preferably also enclosed. Such additional materials are medicine cups, surgical blades, sponges, needle counter, gloves, markers, labels, suture bag, and suction tubing and tip. To complete the kit, a drape is wrapped therearound to enclose the materials in the kit and maintain them in sterile condition. Furthermore, the inside of the wrap or drape is sterile so that when it is unfolded over a back table or ring stand, it serves as a sterile drape.

FIGS. 6, 7, 8 and 9 show progressive steps in the wrapping of the kit. Surgical kit 22 may have selected contents, as previously described. The kit includes as its outer member a basin, and preferably two nested basins. The kit is placed on wrap 78, which serves to enclose the kit, maintain the sterility of the kit, and ultimately serve as a sterile drape. Wrap 78 has near and far edges 80 and 82, left and right edges 84 and 86, sterile top surface 88, and outer surface 90. The outer surface 90 is identified in that manner because a portion thereof will be the outer surface of the completed wrap. It will also be the under surface of the drape.

The width of the drape from the near edge to the far edge is sufficient that when the drape is placed on a ring stand, it adequately drapes over the front and back of the stand, but is not sufficiently wide so as to touch or be close to the floor. If it touches the floor or is near to the floor, it is considered to be contaminated. Similarly, the length of the drape from the left edge 84 to the right edge 86 is sufficient to cover a double ring stand and adequately hang down on the left and right to cover the ring stand but not reach close to the floor. If this same drape is used on a single ring stand, then the left and right edges would be too close to the floor, and such size would be contra-indicated in aseptic technique. Fold lines 92 and 94 permit the drape to be folded under, as seen from the transition from FIG. 6 to FIG. 7, to shorten the effective length from left edge to right edge. In FIG. 7, kit, 22 is projected above the surface of the folded drape; and, in FIG. 7, it is positioned exactly over the center of the folded drape. The fold lines 92 and 94 are spaced apart about half the diameter of a ring in the ring stand so that when folded in this manner and centered on a single ring stand, the left and right edges 84 and 86 are a suitable distance apart, with the shortening fold in place, as shown in FIG. 7, to properly drape a single ring stand.

The kit is placed on the center of the wrap 78, with the shortening fold in place, and the portion forward of fold line 96 is folded back over the kit. Thereupon, the portion of the wrap rearward of fold line 98 is folded forward. Now, all of the sterile surfaces are enclosed, and the structure appears as is shown in FIG. 8. Next, first the right end is folded up to the edge of the basin to fold line 100 and then refolded on itself over the top of the basin toward the left. Next, first the left end is folded up to the edge of the basin to fold line 100 and then re-folded on itself over the top of the basin toward the right and covering the right fold. A seal 104 is applied, and the structure is as shown in FIG. 9. In this configuration, it is first sterilized by radiation and then is stored, distributed, stocked and ultimately delivered to the operating room for use.

When delivered to the operating room, it may be used in a single ring stand, a double ring stand, or on a back table. As a first illustration of use, it is used with a single ring stand 10, as is shown in FIG. 9. The kit is placed in the ring stand, as is shown in FIG. 10, and unwrapped proceeds in the traditional manner of a back table cover folded wrap. As is seen in FIG. 10, the kit is placed in the ring stand, the seal is broken, and the wrap is unfolded completely to the left. Thereupon, the wrap is completely unfolded to the right, and this is a condition seen in FIG. 11. Next, the nurse folds the far edge 82 up and back, away from the nurse, to drape behind the ring stand. FIG. 12 illustrates the intermediate step when the far edge is being unfolded away. From the illustration of FIG. 12, the far edge is folded back. This is the first time in the unwrapping that the sterile top surface 88 is exposed. The nurse should avoid touching the sterile surface 88 and only handle that portion of the drape near its edge. Next, the near edge 80 is unfolded towards the nurse and carried out and down over the front of the ring stand so that the sterile surface 88 is exposed and the ring stand is draped. The kit is accessible for use. The sterile nurse unpackages the kit and distributes the various components, as required. All of the components are disposable, and after the operation, are collected and disposed of, preferably in an aseptic manner.

Double ring stand 106 are seen in FIGS. 14, 15, 16, 17 and 18. Double ring stand 106 is similar to single ring stand 10, except for the presence of two rings, 108 and 110, see FIG. 18. The wrapped kit 14 is placed in ring 108, as seen in FIG. 14. The seal is broken and the wrap, which is the same wrap 78, is unfolded one fold to the left, stopping at the first fold. The left-hand side is not completely unfolded. Next, the nurse grasps the still partially wrapped kit 22, and particularly its basin, in the right hand and grasps the left portion of the wrap in the left hand. In this position, the nurse gently pulls the drape to the left to extend it to the left. This unfolds the shortening folds 92, 94 to provide adequate leftward length to adequately cover the left end of the double ring stand. With the shortening fold unfolded, the left end is completely unfolded down over the ring stand, to the dashed line position shown in FIG. 15. The right side of the drape is unfolded, as previously described, so the left and right edges hang down on the left and right ends of the double ring stand. Thereupon, the far edge 82 is lifted and folded back, and the front edge 80 is lifted forward and draped down over the double ring stand, as shown in FIG. 17. The nurse unfolding the wrap so that it becomes a drape is careful not to touch the top surface 88. The entire kit 22 rests in the right ring 108 of the ring stand, and at this juncture, the sterile nurse transfers the contents of the kit. The lower basin 30 remains in the right ring stand while the upper basin 20 is moved to the left ring stand, as seen in FIGS. 17 and 18. The sterile nurse also distributes the remainder of the contents of the kit, as required.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A pitcher comprising:
   continuous side walls and a bottom attached to said side walls so as to form a closed bottom, continuous side walled, open topped pitcher, said side walls having a top edge where said pitcher is open-topped and said side walls having a bottom edge where said side walls are joined to said bottom;
   said side walls being configured so that they are tapered so as to be smaller adjacent said bottom than adjacent said top edge so that two of said pitchers can be nested, one inside the other, said side walls being symmetrical about a vertical center plane which is substantially normal to said bottom, a first portion of said side walls being curved on a radius which is larger than half the distance across said upper edge so that said first portion of said side walls join at said center plane to form a pointed spout, said side walls having a second portion which is curved on a radius which is smaller than half the distance across said upper edge of said side walls so that where said second curved portion of said side walls adjoin at said center plane, said side walls define an inwardly directed point, said first portion and said second portion of said side walls being substantially tangent to each other; and
   means on said second portion of said side walls for defining grasp surfaces so that said pitcher can be manually grasped on said grasp surfaces for raising said pitcher and pouring from said pitcher out of said first point of said pitcher.

2. The pitcher of claim 1 wherein said means for grasping includes a roughened surface attached to said second portion of said side walls adjacent said upper edge thereof and facing in the same direction as said side walls so that manual grasp of said surface aids in grasp of said pitcher.

3. The pitcher of claim 2 wherein said roughened surface is a first, upwardly facing roughened surface and there is also a second, downwardly facing roughened surface therebelow so that both said surfaces may be grasped for engaging said pitcher.

4. The pitcher of claim 3 wherein said second roughened surface is formed on a wall indented into said pitcher interiorly of said wall portions.

5. The pitcher of claim 4 wherein said second surface is defined by side wall portions positioned inwardly from said second side wall portions and a bottom portion positioned above said bottom so as to define a recess interiorly of said second side wall portions and above said bottom.

6. The pitcher of claim 5 wherein said first roughened surface is on a flange extending outwardly from said second portion of said side walls.

7. The pitcher of claim 6 wherein said pitcher is made of transparent material and has graduations formed on at least one side wall portion thereof.

8. The pitcher of claim 3 wherein both said surfaces are adjacent said center plane and are symmetrical across said center plane.

9. The pitcher of claim 7 wherein said inwardly directed point between said second portions of said side walls is between said grasped surfaces so that fingers engaging in grasp can determine the symmetrical center line of said pitcher by tactile sensing of said point.

10. The pitcher of claim 9 wherein said first roughened surface is on a flange extending outwardly from said second portion of said side walls.

11. The pitcher of claim 9 wherein said pitcher is made of transparent material and has graduations formed on at least one side wall portion thereof.

12. A surgical kit comprising:
a circular basin having tapered side walls of a first radius and having a closed bottom;
a kidney-shaped pan within said basin, said kidney-shaped pan having tapered side walls and having a bottom, said tapered side walls including a first, convex side wall having a first radius so that said first convex side wall fits within and against the side wall of said basin, said kidney-shaped pan having a second concave side wall of a second radius;
a pitcher within said kit, said pitcher having tapered side walls and having a closed bottom, said pitcher being symmetrical about a center plane and having a portion of its side walls formed at said first radius so as to fit within said basin and a portion of its side walls at said second radius so as to fit against said concave side wall of said kidney-shaped pan, said kidney-shaped pan and said pitcher being sized to substantially engage together and fit within said basin.

13. The kit of claim 12 further including
means on said pitcher for manual grasp of said pitcher.

14. The kit of claim 13 wherein said means for grasping includes a roughened surface attached to said second portion of said side walls adjacent said upper edge thereof and facing in the same direction as said side walls so that manual grasp of said surface aids in grasp of said kit.

15. The kit of claim 14 wherein said roughened surface is a first, upwardly facing roughened surface and there is also a second, downwardly facing roughened surface therebelow so that both said surfaces may be grasped for engaging said kit.

16. The kit of claim 15 wherein both said surfaces are adjacent said center plane and are symmetrical across said center plane.

17. The kit of claim 16 wherein said inwardly directed point between said second portions of said side walls is between said grasped surfaces so that fingers engaging in grasp can determine the symmetrical center line of said kit by tactile sensing of said point.

18. The kit of claim 15 wherein said second roughened surface is formed on a wall indented into said kit interiorly of said wall portions.

19. The kit of claim 18 wherein said second surface is defined by side wall portions positioned inwardly from said second side wall portions and a bottom portion positioned above said bottom so as to define a recess interiorly of said second side wall portions and above said bottom.

20. The kit of claim 19 wherein said first roughened surface is on a flange extending outwardly from said second portion of said side walls.

* * * * *